United States Patent [19]

Chang et al.

[11] Patent Number: 4,467,133
[45] Date of Patent: Aug. 21, 1984

[54] CONVERSION OF ALCOHOLS AND ETHERS TO DISTILLATE RANGE HYDROCARBONS

[75] Inventors: Clarence D. Chang, Princeton; William H. Lang, Pennington, both of N.J.

[73] Assignee: Mobil Oil Corporation, New York, N.Y.

[21] Appl. No.: 390,087

[22] Filed: Jun. 21, 1982

[51] Int. Cl.$^3$ .............................................. C07C 1/00
[52] U.S. Cl. ................................... 585/733; 585/469; 585/640
[58] Field of Search ........................ 585/640, 733, 469

[56] References Cited

U.S. PATENT DOCUMENTS

| | | | |
|---|---|---|---|
| 3,140,249 | 7/1964 | Plank et al. | 208/120 |
| 3,140,253 | 7/1964 | Plank et al. | 208/120 |
| 3,556,988 | 1/1971 | Stover et al. | 208/120 |
| 3,928,483 | 12/1975 | Chang et al. | 585/322 |
| 3,969,426 | 7/1976 | Owen et al. | 585/323 |
| 3,979,472 | 3/1976 | Butter | 585/408 |
| 4,013,732 | 3/1977 | Chang et al. | 585/408 |
| 4,035,430 | 7/1977 | Dwyer et al. | 585/322 |
| 4,052,472 | 10/1977 | Givens et al. | 585/469 |
| 4,138,440 | 2/1979 | Chang et al. | 585/640 |
| 4,138,442 | 2/1979 | Chang et al. | 585/408 |
| 4,156,698 | 5/1979 | Dwyer et al. | 585/408 |
| 4,347,397 | 8/1982 | Dwyer et al. | 585/469 |

OTHER PUBLICATIONS

Adv. Catal. 18, 259, (1968).

*Primary Examiner*—Delbert E. Gantz
*Assistant Examiner*—Cynthia A. Prezlock
*Attorney, Agent, or Firm*—A. J. McKillop; M. G. Gilman; L. G. Wise

[57] ABSTRACT

A process for the conversion of alcohols and/or ethers to diesel fuel hydrocarbon mixtures comprising contacting alcohols and/or ethers with large pore zeolites, such as rare-earth Y aluminosilicate under elevated pressures and temperatures below about 600° F.

4 Claims, No Drawings

CONVERSION OF ALCOHOLS AND ETHERS TO DISTILLATE RANGE HYDROCARBONS

BACKGROUND OF THE INVENTION

This invention relates to a process for effecting the conversion of alcohols and/or ethers to distillate range hydrocarbons and more particularly to improvements in the zeolite catalytic conversion of alcohols and/or ethers to produce $C_{10}+$ hydrocarbons.

With the advent of fossil fuel shortages and the accelerated demand for petroleum derived products, there has been an ever increasing demand for synthetic means of providing hydrocarbons, useful as fuel components.

Recently, much effort has been devoted to the synthetic conversion of alcohols, such as methanol, to gasoline range hydrocarbons. One means which has proven successful involves the use of zeolites as catalysts for such conversion reactions. Among these processes are those disclosed in U.S. Pat. Nos. 3,928,483, 4,138,442, 4,013,732, 4,138,440, 3,979,472, and 4,035,430. Others include U.S. Pat. No. 4,156,698 which discloses employing an improved zeolite catalyst in a rare-earth matrix in the conversion process.

Concomitant with the shortage of fossil fuel and the rising costs of gasoline, utilization of diesel fuels has been ever increasing too. Accordingly, recent efforts have been given to the development of improved processes for the production and upgrading of diesel fuel products. While advances have been made in the production and upgrading of diesel fuel, further processes are obviously welcome. Moreover, process for the production of diesel fuel, wherein inexpensive starting materials, such as alcohol, can be employed are preferably desired.

SUMMARY OF THE INVENTION

Accordingly, it is one object of the present invention to provide a process for the production of distillate range ($C_{10}+$) hydrocarbons.

Another object of this invention is to provide a novel process for the conversion of alcohols and/or ethers to distillate range hydrocarbons.

A further object of this invention is to provide a simple and direct one-step process for the production of distillate range hydrocarbons from alcohols and/or ethers.

A still further object of the present invention is to provide a process for the production of a distillate range hydrocarbon product which is suitable as a diesel fuel.

These and other objects are achieved herein by a process which comprises contacting a feed comprising an alcohol and/or an ether, with a large pore zeolite catalyst, under conditions of temperature and pressure sufficient to produce $C_{10}+$ hydrocarbons.

DETAILED DESCRIPTION OF THE INVENTION

In accordance with the present invention, it has been surprisingly discovered that alcohols and/or ethers can be converted to distillate range ($C_{10}+$) hydrocarbons by contact with large pore zeolite catalysts under certain conditions of temperature and pressure.

Thus, for the purposes of this invention, compositions comprising monohydric alcohols having from 1 to 4 carbon atoms may be used as feed to be converted by the process herein. More specifically, among the alcohols contemplated are included methanol, ethanol, n-propanol, isopropanol, n-butanol, sec-butanol and isobutanol alone or in admixture with each other. Moreover, ethers derived from these alcohols are contemplated as feed in the present process too. Thus, ethers used herein include alone or in admixture with themselves or in admixture with the heretofore described alcohols, dimethylether, diethylether, dipropylether and dibutylether, as well as mixed ethers such as methylethyl ether. Particularly preferred feeds are methanol, dimethyl ether and mixtures thereof.

The zeolite catalysts which are employed in the present process are generally defined as large pore zeolites having pore dimensions greater than about 6 angstrom units and pore windows of about a size such as would be provided by 12-membered rings of oxygen atoms.

The zeolites useful in the present process have a structure which provides access to larger molecules. Rather than attempt to judge from crystal structure whether or not a catalyst possesses the necessary access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e. 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of hexane remaining})}{\log_{10}(\text{fraction of 3-methylpentane remaining})}$$

The constraint index approximates the ratio of the cracking rate constants for the two hydrocarbons.

Catalysts suitable for the present invention are those having a constraint index of less than about 1.

Representative crystalline aluminosilicates suitable for the present invention include those natural and synthetic crystalline aluminosilicates having uniform pores of a diameter preferably greater than about 6 angstrom units. Such crystalline aluminosilicates include zeolites Y, X, beta, L, ZSM-4, ZSM-12, ZSM-20, ZSM-50, as well as naturally occuring zeolites including faujasite, mordenite, offretite, gmelinite, and the like. Preferred crystalline aluminosilicates include synthetic faujasite or zeolites X and Y, with particular preference being accorded zeolite Y.

The crystalline aluminosilicates employed herein are essentially characterized by a high catalytic activity. This high catalytic activity may be imparted to the catalyst particles by base exchanging alkali metal aluminosilicate particles with a base-exchange solution containing ions selected from the group consisting of cations of elements of Group IB-VIII of the Periodic Table, hydrogen, and hydrogen precursors, including mixtures thereof with one another. Hydrogen precursors, such as ammonia and ammonium salts, typically undergo, upon heating, degradation to hydrogen cations in contact with aluminosilicates. Suitable methods of base exchange are described in U.S. Pat. Nos. 3,140,249 and 3,140,253.

Where an alkali metal aluminosilicate is employed initially, it is essential to base exchange either the aluminosilicate particles to reduce the sodium content of the final product to less than about 4% by weight and preferably less than 1% by weight.

As previously discussed, base exchange may be accomplished by one or more contacts with a solution containing ions selected from the group consisting of cations of the elements of Groups IB-VIII, hydrogen and hydrogen precursors, including mixtures thereof with one another.

It is most preferred herein that the crystalline aluminosilicate be a rare earth zeolite, that is a crystalline aluminosilicate composition containing rare earth metal cations as a result of treatment with a fluid medium, preferably a liquid medium, containing at least one rare earth metal cation. Rare earth metal salts represent the source of rare earth cation. The product resulting from treatment with a fluid medium is an activated crystalline and/or crystalline-amorphous aluminosilicate in which the structure thereof has been modified primarily to the extent of having the rare earth cations chemisorbed or ionically bonded thereto. These rare-earth zeolite catalysts employed herein are distinct from the composite catalysts of heretofore-mentioned U.S. Pat. No. 4,156,698 which are a composite of a zeolite in a matrix, particularly a rare earth metal containing matrix.

Water is the preferred solvent for the cationic salt, e.g., rare earth metal salt, for reasons of economy and ease of preparation in large scale operations involving continuous or batchwise treatment. Similarly, for this reason, organic solvents are less preferred but can be employed providing the solvent permits ionization of the cationic salt. Typical solvents include cyclic and acyclic ethers such as dioxane, tetrahydrofuran, diethyl ether, diisopropyl ether, and the like; ketones, such as acetone and methyl ethyl ketone; esters such as ethyl acetate; alcohols such as ethanol, propanol, butanol, etc.; and miscellaneous solvents such as dimethylformamide, and the like.

In carrying out the treatment with the fluid medium, the procedure employed varies depending upon the particular aluminosilicate which is treated. If the aluminosilicate which is treated has alkali metal cations associated therewith, then the treatment with the fluid medium or media should be carried out until such time as the alkali metal cations originally present are substantially exhausted. Alkali metal cations, if present in the treated aluminosilicate, tend to suppress or limit catalytic properties, the activity of which, as a general rule, decreases with increasing content of these metallic cations. On the other hand, if the aluminosilicate which is treated with the desired fluid medium is substantially free of alkali metal cations, i.e., a calcium aluminosilicate, then the treatment need not be carried out until such time as the metal is exhausted since the presence of metals other than alkali metals does not seriously limit catalytic properties. Effective treatment with the fluid medium to obtain a modified aluminosilicate having high catalytic activity with vary, of course, with the duration of the treatment and the temperature at which the treatment is carried out. Elevated temperatures tend to hasten the speed of treatment whereas the duration thereof varies inversely with the general concentration of ions in the fluid medium. In general, the temperatures employed range from below ambient room temperature of 24° C. up to temperatures below the decomposition temperature of the aluminosilicate. Following the fluid treatment, the treated aluminosilicate is washed with water, preferably distilled water, until the effluent wash water has a pH value of wash water, i.e., between 5 and 8. The aluminosilicate materials is thereafter analyzed for metallic content by methods well known in the art. Analysis also involves analyzing the effluent wash for anions obtained in the wash as a result of the treatment, as well as determination of and correction for anions that pass into the effluent wash from soluble substances, or decomposition products of insoluble substances, which are otherwise present in the aluminosilicate as impurities.

The treatment of the aluminosilicate with the fluid medium or media may be accomplished in a batchwise or continuous method under atmospheric, superatmospheric or subatmospheric pressures. A solution of rare earth metal cations in the form of a molten material, vapor, aqueous or non-aqueous solution may be passed slowly through a fixed bed of aluminosilicate. If desired, hydrothermal treatment or corresponding non-aqueous treatment with polar solvents may be effected by introducing the aluminosilicate and fluid medium into a closed vessel maintained under autogeneous pressure. Similarly, treatments involving fusion or vapor phase contact may be employed.

Where a rare earth zeolite is desired, a wide variety of rare earth compounds can be employed with facility as a source of rare earth ions. Operable compounds include rare earth chlorides, bromides, iodides, carbonates, bicarbonates, sulfates, sulfides, thiocyanates, peroxysulfates, acetates, benzoates, citrates, nitrates, formates, propionates, butyrates, valerates, lactates, malonates, oxalates, palmitates, hydroxides, tartrates, and the like. The only limitation on the particular rare earth metal salt or salts employed is that it be sufficiently soluble in the fluid medium in which it is used to give the necessary rare earth ion transfer. The preferred rare earth salts are the chlorides, nitrates and sulfates.

Representative of the rare earth metals are cerium, lanthanum, praseodymium, neodymium, samarium, europium, gadolinium, terbium, dysprosium, holmium, erbium, thulium, scandium, yttrium, and lutecium.

The rare earth metal salts employed can either be the salt of a single rare earth metal or mixtures of rare earth metals, such as rare earth chlorides of didymium chlorides. A rare earth chloride solution is a mixture of rare earth chlorides consisting essentially of the chlorides of lanthanum, cerium, neodymium and praseodymium with minor amounts of samarium, gadolinium and yttrium. Rare earth chloride solutions are commercially available and for example contain the chlorides of the rare earth mixture having the relative composition cerium (as $CeO_2$) 48% by weight, lanthanum (as $La_2O_3$) 24% by weight, praseodymium (as $Pr_2O_3$) 5% by weight, neodymium (as $Nd_2O_3$) 17% by weight, samarium (as $Sm_2O_3$) 3% by weight, gadolinium (as $Gd_2O_3$) 2% by weight, and other rare earth oxides 0.8% by weight. Didymium chloride is also a mixture of rare earth chlorides but having a lower cerium content. It consists of the following rare earths determined as oxides: lanthanum 45–56% by weight, cerium 1–2% by weight, praseodymium 9–10% by weight, neodymium 32–33% by weight, samarium 5–7% by weight, gadolinium 3–4% by weight, yttrium 0.4% by weight, and other rare earths 1–2% by weight. It is to be understood that other mixtures of rare earth are also applicable, although lanthanum, neodymium, praseodymium, samarium and gadolinium as well as mixtures of rare earth cations containing a predominant amount of one or more of the above cations are preferred.

Aluminosilicates which are treated with a fluid medium or media in the manner above described include a wide variety of aluminosilicates both natural and synthetic which have a crystalline or combination of crystalline and amorphous structure.

The aluminosilicates can be described as a three-dimensional framework of $SiO_4$ and $AlO_4$ tetrahedra in which the tetrahedra are cross-linked by the sharing of oxygen atoms whereby the ratio of total aluminum and silicon atoms to oxygen atoms is 1:2. In their hydrated form, the aluminosilicates may be represented by the formula:

$$M_{2/n}O:Al_2O_3:wSiO_2:YH_2O$$

wherein M represents at least one cation which balances the electrovalence of the tetrahedra, n represents the valence of the cation, w the moles of $SiO_2$ and Y the moles of $H_2O$. The cations can be any or more of a number of metal ions, depending upon whether the aluminosilicate is synthesized or occurs naturally. Typical cations include sodium, lithium, potassium, silver, magnesium, calcium, zinc, barium, iron, nickel, cobalt and manganese. Although the proportions of inorganic oxides in the silicates and their spatial arrangements may vary affecting distinct properties in the aluminosilicate, the main characteristic of these materials is their ability to undergo dehydration without substantially affecting the $SiO_4$ and $AlO_4$ framework.

Aluminosilicates falling within the above formula are well known and, as noted, include synthesized aluminosilicates, natural aluminosilicates, and certain caustic treated clays. Among the aluminosilicates are included zeolites, Y, L, S, X, levynite, erionite, faujasite, analcite, paulingite, noselite, phillipsite, datolite, gmelinite, leucite, scapolite, mordenite as well as certain caustic treated clays such as montmorillonite and kaolin families. The preferred aluminosilicates are those having pore diameters of greater than about 6 angstroms.

Particularly preferred rare earth zeolites for use in this invention may be made by base exchange of sodium zeolite X with rare earth ions to form rare earth zeolite X and by base exchange of sodium zeolite Y with rare earth ions to form rare earth zeolite Y.

It has been discovered herein that certain conditions of temperature and pressure are essential to the conversion of the alcohol and/or ether feed to distillate range hydrocarbons. That is, it has been found herein that the conversion to distillate range hydrocarbons takes place under conditions of elevated pressure and relatively low temperature. More particularly, the elevated pressures contemplated within the scope of the present invention are within the range of from about 5 to about 200 atmospheres while the temperatures found essential to the conversion are below about 600° F. The results found herein are particularly surprising and unexpected since the conversion of alcohols, such as methanol over large pore zeolites at atmospheric pressure and at temperatures in excess of 600° F. has been previously found to result in products consisting essentially of light gases and polyalkyl aromatics rather than distillate range hydrocarbons, e.g. consisting essentially of n- or singly branched olefins. Moreover, unlike the results obtained in the present process, under conditions of atmospheric pressure and temperatures in excess of 600° F., the zeolite catalyst aging is very rapid due to coke formation. This prior work is reported, for example, by P. B. Venuto et al., Adv. Catal. 18, 259(1968). Thus, for instance, lowering the pressure from 500 psig to atmospheric, reduces the selectivity to $C_{10}+$ hydrocarbons from nearly 100 percent to zero, whereas the higher temperatures (i.e., above 600° F.) promote cracking and aromatization.

Typically, carrying out the process herein, the hereinbefore described feed of alcohol and/or ethers is brought into contact with the hereinbefore described large pore zeolite catalysts at a temperature below 600° F., preferably from about 25° F. to about 590° F. and most preferably at about 500° F., for a contact time equivalent to or the same as a weight hourly space velocity (WHSV) of about 0.1 to about 100, preferably about 0.3 to about 40, it being understood that WSHV signifies pounds of feed per pound of zeolite per hour; and at a pressure of from about 5 to about 200 atmospheres, preferably from about 10 to about 150 atmospheres, most preferably from about 15 to 100 atmospheres.

As indicated hereinbefore distillate range product resulting from the present process consists essentially of n or singly-branched olefins and is particularly useful as diesel fuel.

In order that those skilled in the art may better understand how the present invention may be practiced, the following examples are given by way of illustration and not by way of limitation.

EXAMPLE 1 AND COMPARATIVE EXAMPLE 1A

Feed: Methanol
Catalyst: REY

| Example | Time-on-Stream, hr. | LHSV, hr.$^{-1}$ | T °F. | P psig |
|---------|---------------------|------------------|-------|--------|
| 1       | 27                  | 0.67             | 500   | 500    |
| 1A      | 49                  | 0.33             | 500   | 0      |

TABLE

| Example | 1 | 1A |
|---------|---|-----|
| Conversion, % ($CH_2$) | 46.5 | 16.4 |
| Hydrocarbons, Wt % | | |
| $C_1$ | trace | 15.7 |
| $C_2$ | " | 0.5 |
| $C_3$ | " | 21.4 |
| $C_4$ | " | 27.5 |
| $C_5$ | " | 10.6 |
| $C_6$–$C_9$ | " | 24.3 |
| $C_{10}$–$C_{20}$ | 71.9 | — |
| $C_{21}$–$C_{29}+$ | 28.1 | — |
| | 100.0 | 100.0 |

The product of Example 1 is seen to consist of $C_{10}$–$C_{29}+$ hydrocarbons, while in comparative Example 1A, the product is $C_9-$, containing a large amount of light gas including methane. Moreover, it is significant to note that in Example 1, the catalyst is still active after 2 days. It has been previously shown that at higher temperatures, the catalyst is deactivated within a few hours.

Substituting other large pore zeolite catalysts and other alcohols and/or ethers, such as ZSM-20 and dimethylether for the REY zeolite catalyst and methanol of Example 1 respectively, provides similar conversion results.

Obviously, other modifications and variations of the present invention are possible in the light of the above teachings. It is, therefore, to be understood that changes may be made in the particular embodiments of this invention which are within the full intended scope of the invention as defined by the appended claims.

What is claimed is:

1. A process for the selective conversion of alcohols or ethers or mixtures thereof to distillate range hydrocarbons said process comprising contacting a feed selected from the group consisting of alcohol, ether and mixtures thereof with a large pore crystalline aluminosilicate zeolite catalyst selected from the group consisting of synthetic faujasite, zeolite X and Zeolite Y at a pressure in the range of from about 5 to about 200 atmospheres and at a conversion temperature below about 600° F.

2. A process for the selective conversion of alcohols or ethers or mixtures thereof to distillate range hydrocarbons said process comprising contacting a feed selected from the group consisting of alcohol, ether and mixtures thereof with a large pore crystalline aluminosilicate zeolite catalyst selected from the group consisting of rare earth zeolite X (REX) and rare earth Zeolite Y (REY) at a pressure in the range of from about 5 to about 200 atmospheres and at a conversion temperature below about 600° F.

3. A process as defined in claim 1 wherein said temperature is about 400° F. and said pressure is about 500 psig.

4. A process as defined in claim 2 wherein said temperature is about 500° F. and said pressure is about 500 psig.

* * * * *